United States Patent
Parodi

(10) Patent No.: US 6,302,908 B1
(45) Date of Patent: *Oct. 16, 2001

(54) ARTERIAL GRAFT DEVICE AND METHOD OF POSITIONING THE SAME

(76) Inventor: Juan Carlos Parodi, Don Bosco 3235, Lomas de San Isidro, 1642, Province of Buenos Aires (AR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/822,858

(22) Filed: Mar. 24, 1997

(51) Int. Cl.[7] ................................................. A61F 2/00
(52) U.S. Cl. ........................................ 623/1.31; 623/1.35
(58) Field of Search ................................. 623/1, 11, 12, 623/1.3, 1.31, 1.35

(56) References Cited

U.S. PATENT DOCUMENTS

| | | | |
|---|---|---|---|
| 3,657,744 | * | 4/1972 | Ersek . |
| 4,140,126 | * | 2/1979 | Choudhury . |
| 4,562,596 | * | 1/1986 | Kornberg . |
| 4,577,631 | * | 3/1986 | Kreamer . |
| 4,787,899 | * | 11/1988 | Lazarus . |
| 5,078,726 | * | 1/1992 | Kreamer . |
| 5,104,399 | * | 4/1992 | Lazarus . |
| 5,219,355 | * | 6/1993 | Parodi et al. . |
| 5,360,443 | * | 11/1994 | Barone et al. . |
| 5,522,880 | * | 6/1996 | Barone et al. . |
| 5,562,724 | * | 10/1996 | Vorwerk et al. .......................... 623/1 |
| 5,571,171 | * | 11/1996 | Barone et al. . |
| 5,571,173 | * | 11/1996 | Parodi . |
| 5,575,817 | * | 11/1996 | Martin ...................................... 623/1 |
| 5,578,071 | * | 11/1996 | Parodi . |
| 5,578,072 | * | 11/1996 | Barone et al. . |
| 5,591,229 | * | 1/1997 | Parodi . |
| 5,609,627 | * | 3/1997 | Goicoechea et al. ..................... 623/1 |
| 5,628,788 | * | 5/1997 | Pinchuk .................................... 623/1 |
| 5,632,763 | * | 5/1997 | Glastra ...................................... 623/1 |
| 5,632,772 | * | 5/1997 | Alcime et al. ............................ 623/1 |
| 5,639,278 | * | 6/1997 | Dereume et al. ......................... 623/1 |
| 5,683,449 | * | 11/1997 | Marcade ............................... 623/1.35 |
| 5,824,037 | * | 10/1998 | Fogarty et al. ........................... 623/1 |
| 5,824,040 | * | 10/1998 | Cox et al. ................................. 623/1 |
| 5,824,042 | * | 10/1998 | Lombardi et al. ........................ 623/1 |
| B1 4,733,665 | * | 1/1994 | Palmaz . |

FOREIGN PATENT DOCUMENTS

| | | |
|---|---|---|
| 0 508 473 A2 | 10/1992 | (EP) . |
| 0 539 237 A1 | 4/1993 | (EP) . |
| WO 98/32399 | 7/1998 | (WO) . |

* cited by examiner

Primary Examiner—Michael J. Milano
(74) Attorney, Agent, or Firm—Ratner & Prestia

(57) ABSTRACT

An arterial graft device and a process for positioning the same, wherein the device comprises a first part positioned by conventional techniques within the artery, and a second part which is positioned and fixed on the first part by a cone-shaped segment which is provided on the first part so as to prevent a catheter guidewire—whereby the second part is positioned in place—from deviating and damaging arterial walls.

7 Claims, 2 Drawing Sheets

ARTERIAL GRAFT DEVICE AND METHOD OF POSITIONING THE SAME

FIELD OF THE INVENTION

This invention refers to techniques for the treatment of aneurysm and preferably to the endoluminal treatment thereof, and more particularly, this invention refers to an arterial graft device and a method for positioning the same. More specifically, this invention refers to an aortic bifurcated endoluminal graft device used in the treatment of infra-renal aortic aneurysm, as well as to a process for positioning such device within the infra-renal aorta and the corresponding iliac arteries.

BACKGROUND OF THE INVENTION

In the field of vascular therapies, the endoluminal treatment of aneurysm is being increasingly implemented, together with the treatment of other occlusive diseases and trauma of arteries. In the particular case of infra-renal aortic aneurysm, a bifurcated graft device is currently used, which comprises at least a stump of the kind comprising a deployable and expandable metal material which is disposed at the level of the infra-renal aorta, including both iliac common arteries. In order to carry out this treatment, a double-system graft device, which basically consists of two components or parts, is typically used. The first part is an aortic main tubular body aimed at endoluminally covering the infra-renal aorta, and which goes through an extension or segment that is to be coupled to one of the iliac arteries. Once this first part or component of the graft device has been positioned by the already known catheterizing techniques, the second part of the device has to be connected, which is formed by a contralateral segment to be connected to a connecting opening of the first part of the device. The contralateral segment will be received within the connecting opening of the said first part of the device and will enter said connecting opening through the guidewire of a catheter directed from the femoral artery of the patient up to the aortic aneurysm cavity. Once there, the second component of the graft device will be carefully and properly connected to the connecting opening of the first component of the said graft device.

Inserting the guidewire and guiding it until the same enters the connecting opening of the graft first component is the most difficult step, since the end of the catheter guide, once inside the aneurysm cavity, lacks any guide leading it directly towards the said connecting opening. When the professional tries to find the connecting opening so as to introduce the distal end of the catheter wire, this end can possibly penetrate the aortic mural thrombus—present in the aneurysm cavity—and can eventually cause disruption of the thrombus and embolism of the visceral arteries and of the lower extremity arteries.

In order to prevent such accidents during a treatment of aneurysm consisting in positioning an endoluminal graft, the inventor has sought a solution through the possibility of safely directing the guidewire of the catheter up to the connecting opening of the graft first component, as well as directing the said second component and having it easily connected to the first component through the corresponding connecting opening.

SUMMARY OF INVENTION

Therefore, it is an object of the present invention to provide an arterial graft device, which is formed by two components safely coupled one to the other once the first component is positioned within the artery to be treated, said device comprising guiding means for a guidewire of a catheter and for the second component to be coupled to the connecting opening of the first component.

Further, it is an object of this invention to provide an arterial graft device of the type comprising two parts to be inserted one at a time within the artery to be repaired and which should be connected one to the other within the artery they enter by means of catheterizing techniques, wherein a first of said parts has a connecting opening where the second part is coupled, said first part comprising guiding means which form a funnel allowing entrance of the catheter guidewire and of the second part of said graft device.

It is yet a further object of this invention to provide a process for positioning an arterial graft device at the place where said first part of the device is inserted and positioned within the artery to be repaired, a catheter guidewire being then inserted therein and said second part of the graft device being thereby carried to the connecting opening so as to be connected to the first part of the graft device, wherein said guidewire is directed towards the artery to be repaired and, when reaching said artery, it is funneled through a coned passage that becomes narrower at the portion thereof near said connecting opening, wherein said second part of the graft device is carried along said guidewire and along said funnel until being connected to said connecting opening of the first part of the graft device.

BRIEF DESCRIPTION OF THE DRAWINGS

For the sake of more clearly understanding the object of this invention, the same has been illustrated by several figures, which represent some of the preferred embodiments of said object, as an example, and, wherein.

DETAILED DESCRIPTION OF THE PREFERRED EMBODIMENT

Figure 1:
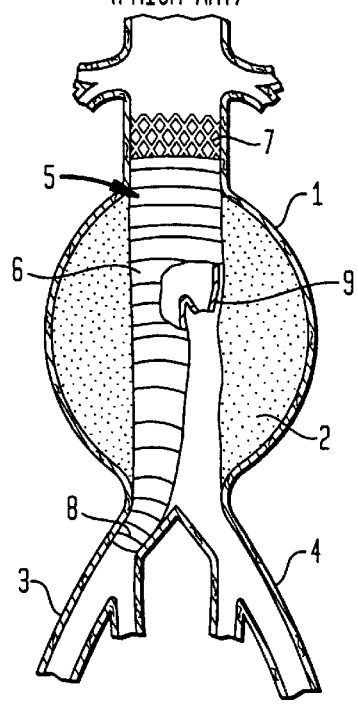
FIG. 1 is a schematic view of the aorta wherein, and by means of conventional techniques, a first component of a graft device has been positioned, said first component having a main part disposed at the infra-renal aortic area and a lower segment inserted within one of the iliac arteries.

FIG. 1 shows a cross-section view of an abdominal aortic aneurysm being repaired according to a conventional graft device. Aorta I shows a mural aneurysm 2, as well as iliac arteries 3 and 4. The graft device 5 comprises a first part or component 6 retained by conventional techniques and an expandable stump device 7 on the artery wall. In this particular case, body 6 endoluminally covering aorta 1 is inserted by segment 8 within die iliac artery 3. The fist component 6 contains a connecting opening 9 aimed at being connected to a second component 10 of the graft device 5 (see FIG. 3) so as to form a bifurcated endoluminal aortic device which covers both the infra-renal aortic level and die two iliac arteries 3 and 4.

Figure 2:
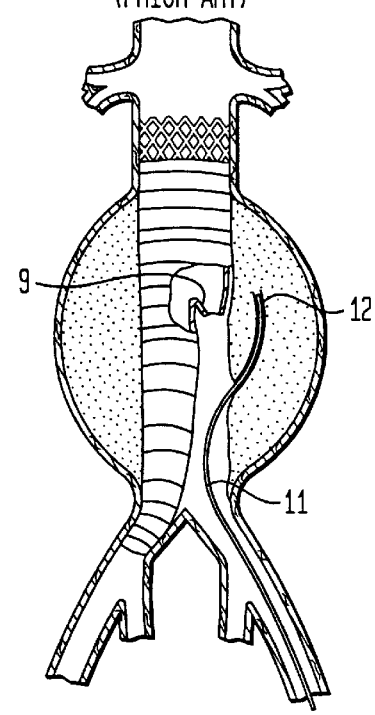
FIG. 2 is a view similar to that of FIG. 1, which shows the end of a guidewire damaging the aortic wall when trying to insert such guidewire within the connecting opening of the first component of said graft device.
Figure 3:
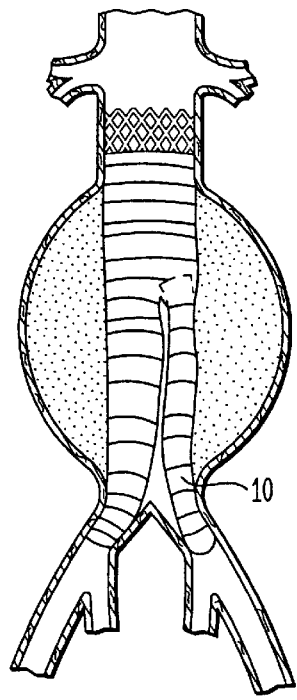
FIG. 3 is an illustration similar to that of FIGS. 1 and 2, which shows the second component of the graft device already connected to the first component of the said device, which is also carried out by a conventional process.
Figure 4:
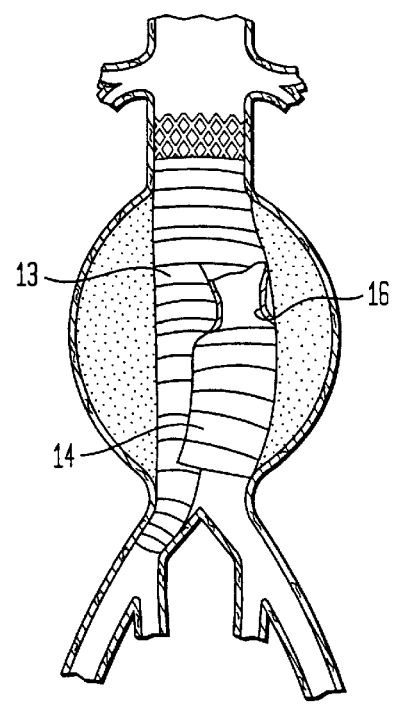
FIG. 4 is a view similar to that of FIGS. 1 to 3, which further shows the first component of the arterial graft including the guiding means, according to the present invention, in the position illustrated in FIG. 1.
Figure 5:
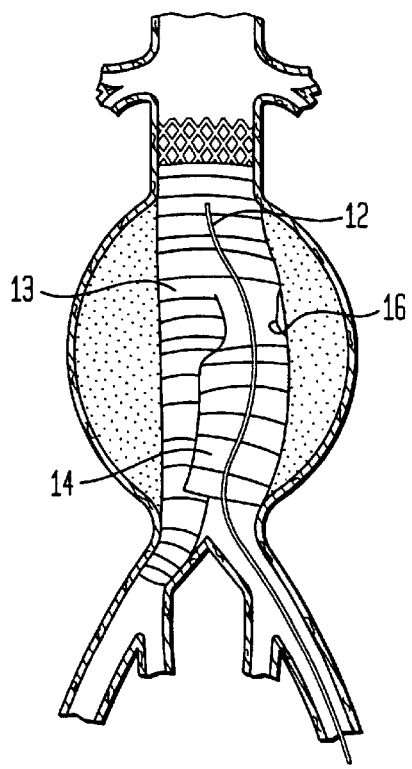
FIG. 5 is similar to FIG. 2, which further shows the guiding means allowing the catheter guidewire to easily enter the connecting opening of the first component of the graft device.
Figure 6:
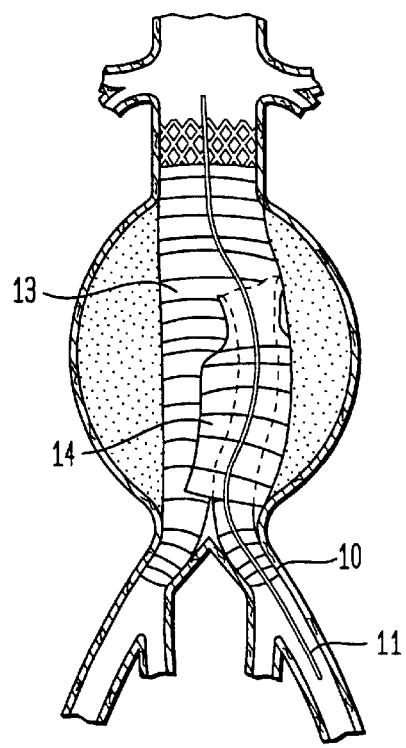
FIG. 6 is a more detailed illustration of the second component being positioned within the connecting opening of the said first component of the device.
Figure 7:
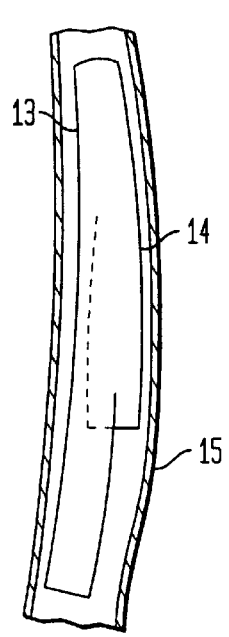
FIG. 7 is an schematic illustration of the first component and the coned vertex being undeployed within a catheter sheath.
Figure 8:
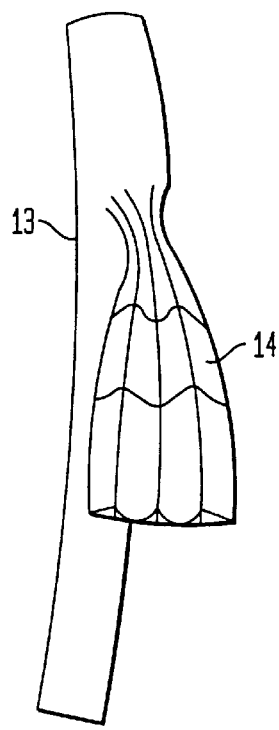
FIG. 8 shows the first component of the graft device with the coned vertex once deployed.

As shown in FIGS. 1 to 3, conventional techniques for assembling an aortic device of this type comprise inserting the first component or part 6 and positioning the same as illustrated in FIG. 1. Once the first component 6 of the aortic device is positioned in place, a catheter is introduced by a guidewire 11 intended to locate connecting opening 9 of die first component 5 of the aortic device. Such as illustrated in FIG. 2, the guidewire cannot be easily inserted within wire 9 and end 12 of the wire can possibly perforate the aortic mural thrombus and cause disruption of die latter, as well as embolism of visceral arteries and low extremity arteries.

According to this invention, die second component 10 of the graft device is positioned by a novel process and by a graft device that prevents guidewire 11—and subsequently end 12 thereof—from perforating the aortic wall or damaging any arterial wall. According to this invention, the first component or part 13 of tie graft device, as illustrated in FIGS. 4 to 8, comprises a vertex or segment 14 which can be folded together with the first component 13 so as to be introduced within a catheter sheath (see FIG. 7) and be directed therein in a conventional manner. Said segment or vertex 14 is, when deployed, slightly cone- or trumpet-shaped, such as more clearly illustrated in FIG. 8, so that when the first component 13 is mounted within the aortic endoluminal cavity, deployed vertex 14 forms a coned passage which guides the catheter guidewire 11 which, as coining from iliac artery 4, easily enters towards connecting opening 16, equivalent to connecting opening 9 of a conventional graft device. As shown by the different sequences of FIGS. 4, 5 and 6, end 12 of the catheter wire 11 easily enters connecting opening 16 and thus allows the second component 10 to enter along guidewire 11 in order to be connected to connecting opening of the first component 13.

The material used for making vertex 14 can be the same material used for component 13 and second component 10 of the graft device. This material can be a plastic material, a compound material, a metallic material and, in general, it can comprise any expansion mechanism, such as balloon expansion, thermal memory, spring loaded elasticity or auto expansion. In general, the preferred material is nitinol, which forms a dacron covered structure, either inside or outside the device. The material can be covered or coated by polyurethane or polytetrafluorocetylene.

It should be clear from the foregoing description that the steps of the process for inserting an aortic graft device such as that of this invention are safer and simpler than the steps of a conventional process, allow the complete assembly of the device in a prompt manner and further prevent any damage to arterial walls, such as caused by conventional processes.

What is claimed is:

1. An arterial graft device for reinforcing bifurcated arteries having a distal main artery portion and two proximal bifurcated legs, the arterial graft device comprising a body and a separate elongated segment, said body including: (i) an expandable retaining device to fix the body into the main artery portion; (ii) an integral elongated segment depending from a bifurcated juncture, the integral depending elongated segment being capable of extending into one of the two legs to internally connect the main artery portion with the one leg; (iii) a cone-shaped segment depending from a connecting opening and extending toward the other leg, the cone-shaped segment having a passage of proximally increasing diameter as the cone-shaped segment extends from the connecting opening toward the other leg for receiving and guiding a catheter guidewire inserted along the other leg and for guiding the separate elongated segment of the graft device for connection with the connecting opening; and (iv) a connecting surface comprising an axially extended inner periphery extending distally with an increasing diameter from the connecting opening toward the bifurcated juncture.

2. The graft device of claim 1 wherein the separate elongated segment further comprises an axially extended and entirely circumferentially extended outer connecting surface adapted to bear upon the connecting surface of said body.

3. The arterial graft device of claim 1, wherein the cone-shaped segment is formed by a foldable structure, which can be compressed and expanded and inserted together with said body within a catheter sheath.

4. The arterial graft device of claim 1, wherein said cone-shaped segment and said body comprise a unitary structure of the same material.

5. The arterial graft device according to claim 4, wherein said material is selected from the group comprising plastic and metal, said device being expandable by any of the following mechanisms: balloon expansion, thermal memory, elasticity, spring-loaded elasticity, and autoexpansion.

6. The arterial graft device according to claim 4, wherein the material is polyethylene or polytetrafluoroethylene.

7. The arterial graft device according to claim 1, wherein the arterial graft device forms a bifurcated aortic endoluminal graft disposed on the infra-renal aorta and the iliac arteries, said integral elongated segment extending into a first iliac artery and said cone-shaped segment extending in the aorta towards a second iliac artery.

* * * * *

UNITED STATES PATENT AND TRADEMARK OFFICE
CERTIFICATE OF CORRECTION

PATENT NO.    : 6,302,908 B1                                              Page 1 of 1
DATED         : October 16, 2001
INVENTOR(S)   : Juan Carlos Parodi It is certified that error appears in the above-identified patent and that said Letters Patent is hereby corrected as shown below:

<u>Title page,</u>
Item [56], References Cited, add the following references under
"U.S. PATENT DOCUMENTS": -- 6,015,431   1/2000   Thornton et al. --

Signed and Sealed this

Sixteenth Day of July, 2002

Attest:

Attesting Officer

JAMES E. ROGAN
Director of the United States Patent and Trademark Office